United States Patent
Larsen (10) Patent No.: US 9,511,163 B2
(45) Date of Patent: Dec. 6, 2016

(54) METHOD OF DISINFECTING ONE OR MORE SURFACES AND/OR STERILIZING AIR, AND AN APPARATUS FOR USE IN THE METHOD

(71) Applicant: JIMCO A/S, Rudkøbing (DK)

(72) Inventor: Jimmy Kjølby Larsen, Rudkøbing (DK)

(73) Assignee: Jimco A/S, Rudkøbing (DK)

( * ) Notice: Subject to any disclaimer, the term of this patent is extended or adjusted under 35 U.S.C. 154(b) by 0 days.

(21) Appl. No.: 14/436,318

(22) PCT Filed: Oct. 19, 2012

(86) PCT No.: PCT/EP2012/070820
§ 371 (c)(1),
(2) Date: Apr. 16, 2015

(87) PCT Pub. No.: WO2014/060051
PCT Pub. Date: Apr. 24, 2014

(65) Prior Publication Data
US 2015/0258234 A1    Sep. 17, 2015

(51) Int. Cl.
| | | |
|---|---|---|
| *A61N 5/00* | (2006.01) |
| *G01N 23/00* | (2006.01) |
| *A62B 7/08* | (2006.01) |
| *A61L 2/20* | (2006.01) |
| *A61L 2/10* | (2006.01) |
| *A61L 2/24* | (2006.01) |
| *A61L 9/015* | (2006.01) |
| *A61L 9/20* | (2006.01) |
| *A61L 9/04* | (2006.01) |
| *A61L 9/12* | (2006.01) |
| *F24F 3/16* | (2006.01) |

(52) U.S. Cl.
CPC ............... *A61L 2/202* (2013.01); *A61L 2/10* (2013.01); *A61L 2/24* (2013.01); *A61L 9/015* (2013.01); *A61L 9/04* (2013.01); *A61L 9/12* (2013.01); *A61L 9/20* (2013.01); *A61L 2202/121* (2013.01); *A61L 2202/14* (2013.01); *A61L 2202/16* (2013.01); *A61L 2202/25* (2013.01); *A61L 2209/111* (2013.01); *A61L 2209/16* (2013.01); *A61L 2209/212* (2013.01); *F24F 2003/1667* (2013.01); *F24F 2003/1671* (2013.01)

(58) Field of Classification Search
CPC ........... A61L 2/00; A61L 2/202; A61L 9/00; A61L 9/20
USPC ........ 422/1, 24, 121, 186; 250/455.11, 492.1
See application file for complete search history.

(56) References Cited

U.S. PATENT DOCUMENTS

| | | | |
|---|---|---|---|
| 2004/0202570 A1 | 10/2004 | Nadkarni | |
| 2005/0123436 A1* | 6/2005 | Cumberland | A61L 2/10 422/5 |

(Continued)

FOREIGN PATENT DOCUMENTS

WO    WO2006095199 A1    9/2006

OTHER PUBLICATIONS

International Search Report and Written Opinion, PCT/EP2012/070820 mailed Aug. 9, 2013.

*Primary Examiner* — Monzer R Chorbaji
(74) *Attorney, Agent, or Firm* — Winston & Strawn LLP (57) ABSTRACT

A method of disinfecting one or more surfaces and an apparatus for use in the method. The method includes a securing step arranged for creating an isolation of the surfaces to be disinfected, a disinfection step for emitting UV radiation for the generation of ozone and/or for the sterilization of air from one or more ultra violet (UV) light sources, and adding the generated ozone to the isolation, and a termination step arranged for terminating the generation of ozone and terminating the securing step.

23 Claims, 2 Drawing Sheets

(56) References Cited

U.S. PATENT DOCUMENTS

2005/0186108 A1  8/2005  Fields
2008/0310992 A1  12/2008  Heselton et al.
2009/0180934 A1  7/2009  Khoshbin
2010/0178196 A1  7/2010  Garner

* cited by examiner

METHOD OF DISINFECTING ONE OR MORE SURFACES AND/OR STERILIZING AIR, AND AN APPARATUS FOR USE IN THE METHOD

CROSS REFERENCE TO RELATED APPLICTIONS

This application is a 371 filing of International Patent Application PCT/EP2012/070820 filed Oct. 19, 2012.

BACKGROUND

The present invention relates to a method of disinfecting one or more surfaces and/or sterilizing air, and an apparatus for use in said method.

In industrial kitchens, in air conditioning systems and in the hospital sector it is known that frequent cleaning and disinfection is a requirement. However, conventional cleaning with soap, water and disinfecting detergent chemicals is often not sufficient. Alternative cleaning agents have to be applied, and particularly ozone ($O_3$) has proven to be successful.

Ozone has long been recognized as a useful gas/chemical commodity valued particularly for its outstanding oxidative activity. Because of this activity it finds wide application in disinfection processes. In fact, it kills bacteria/vira/mould more rapidly than chlorine, it decomposes organic molecules, and removes coloration in aqueous systems. Ozonation removes cyanides, phenols, iron, maganese, and detergents. It controls biofilm formation in aqueous systems, yet maintains a high oxygen content in the system. Unlike chlorination, which leaves undesirable chlorinated organic residues in organic containing systems, ozonation leaves fewer potentially harmful residues. There is evidence that ozone also is capable of destroying viruses. It is used for sterilization in the brewing industry and for odor control in sewage treatment and manufacturing.

Thus, ozone has widespread application in many diverse activities, and its use would undoubtedly expand if its cost of production could be reduced. In addition, since ozone is explosive when concentrated as either a gas or liquid, or when dissolved into solvents, its transportation is potentially hazardous. Therefore, it is generally manufactured on the site where it is used. However, the cost of generating equipment, and poor energy efficiency of production has deterred its use in many applications and in many locations.

On a commercial basis, ozone is often produced by the silent electric discharge process, otherwise known as corona discharge, wherein air or oxygen is passed through an intense, high frequency alternating current electric field.

Another way of producing ozone is by use of UV radiation. UV radiation is characterised by waves, with a wavelength in the area of 10 nm to 380 nm. UV radiation is typically divided into three different subgroups UV-A, UV-B and UV-C, with wavelengths of approximately 320-380 nm, 280-320 nm and 100-280 nm, respectively. UV-C radiation is known to destroy most organic molecules and is e.g. used in the hospital sector for sterilising medical equipment. However, at wavelengths of 100 nm to 240 nm, UV radiation is known to produce ozone from oxygen ($O_2$) for example contained in air.

However, even though generation of ozone using corona discharge is extremely expensive it is conventionally considered as the only possible way of generating sufficient ozone for disinfecting purposes.

Due to it's strong oxidising effect, ozone is however also hazardous to humans even at low concentrations, as it causes injury on the respiratory system. Today's methods of disinfecting by use of ozone thus continuously have to be improved in regards to safety.

Attempts have been made to develop a successful and safe disinfection. US2006/0263276A1 relates to a mobile ozone generating apparatus for disinfecting an isolated room. The apparatus comprises among others more openings, at least one UV lamp and a ventilator. With use of a remote controller and a timer the apparatus can be turned on and off from a distance. The ventilator moves air from the isolated room into the apparatus and close to the at least one UV lamp. The air is thus irradiated by the UV lamp resulting in the production of ozone. The air now containing a larger concentration of ozone is then released to the room. It is stated that the concentration of ozone can be increased by increasing the number of UV lamps or alternatively the flow rate of air through the apparatus. The primary target of using the apparatus is to disinfect the air in the room. However, it is stated that the apparatus is also used for disinfect surfaces in the room at higher ozone concentrations. Finally, the apparatus can be equipped with more outlets so that more rooms can be disinfected simultaneously.

WO2006/095199A1 relates to an apparatus for removing unpleasant odour and impurities from air and for preventing impurities in accumulating on surfaces. The apparatus consists of two sections, a first section through which air is flown and added ozone, and a second section through which the air subsequently flows, and where excess ozone is converted into oxygen. The two sections of the apparatus are placed with a distance to each other for example in the tubes of a ventilation system, but can also be a mobile separate apparatus having it's own tube system. The ozone can be produced and added to the air in the first section by irradiating the air with UV radiation from one or more UV lamps with a wavelength of preferably 185 nm. Alternatively, the ozone can be produced from air outside the tube system and subsequently added to the air inside the tube system.

Known apparatuses and methods for disinfecting surfaces and/or sterilizing air do thus not present a simple and effective safety system to minimise health risks for persons using the apparatuses. Furthermore, the known apparatuses are not simple, economical and convenient to use. Additionally, they are not capable of producing the desired high concentration of ozone from ambient air capable of sterilising all the required surfaces.

SUMMARY OF THE INVENTION

The above-mentioned disadvantage and inconvenience of the prior art methods of and apparatuses for disinfecting surfaces and/or sterilizing air are according to the method remedied by, In a first aspect of the invention providing a method of the type mentioned in the opening paragraph, which is easy to use, In a second aspect of the invention providing a method of the type mentioned in the opening paragraph, which is low cost and has low energy consuming in both production and operation, In a third aspect of the invention providing a method of the type mentioned in the opening paragraph, which provides high safety, In a fourth aspect of the invention providing a method of the type mentioned in the opening paragraph, which provides a complete and effective disinfection of surfaces, In a fifth aspect of the invention providing an apparatus which facilitates the method according to the present invention, in a sixth aspect of the invention providing an alternative method and apparatus to the known methods and apparatuses mentioned in the opening paragraph.

The novel and unique features whereby these and other aspects are achieved according to the present invention consists in the fact that the method comprises a securing step arranged for creating an isolation containing the surfaces and/or air to be disinfected and/or sterilised, a disinfection/sterilisation step comprising emitting UV radiation for the generation of ozone, from one or more ultra violet (UV) light sources thus and adding the generated ozone to said isolation, and a termination step arranged for terminating the generation of ozone and terminating the securing step.

DETAILED DESCRIPTION OF THE INVENTION

Within the context of the present patent application the term "UV light source" is to be understood as e.g. a UV lamp, a germicidal low, medium or high pressure lamp, a light-emitting diode (LED), or similar emitting UV radiation with a wavelength capable of generating ozone and/or for sterilizing air.

In the present invention the term "isolation" means any space which can be securely closed, e.g. a room, a refrigerator, a ventilation duct etc. The only requirement is that the isolation can be closed off from the surroundings, such that the ozone is contained in said isolation during the disinfections period, for example by creating an underpressure in said isolation to prevent ozone from escaping to the surroundings.

One huge advantage of applying said three separated steps according to the invention is that they result in a simple, effective and most importantly safe way of disinfecting one or more surfaces (for example removing biofilm). By firstly isolating the surfaces the user of the apparatus makes sure that no one is present in the isolation when initiating the disinfection step, and very important that no one will enter the isolation by mistake during the disinfection step, which is crucial as high ozone concentrations (>0.1 ppm) are hazardous to humans. Preferably, the disinfection method is initiated by use of e.g. a remote control, so that the user is positioned outside the isolation when the disinfection step is initiating, to minimise the risk of being exposed to ozone, however in a different embodiment the method can be initiated by other means. The termination step ensures that no ozone is generated after disinfection is completed, and after the securing step is terminated thus reducing expenses minimising health risks.

The disinfection step can also comprise emitting UV radiation for the sterilization of air from one or more ultra violet (UV) light sources. The one or more UV light sources can thus emit radiation arranged both for disinfecting surfaces, via ozone and for sterilizing air via ozone and/or UV light in the isolation while simultaneously having securing means monitor trespassing. If the isolation for example is a room containing vegetables and/or fruits said combination of UV radiation can minimise ethylene concentration by photochemical oxidation and thus e.g. minimise decomposition.

Advantageously, the securing step can comprise continuously monitoring trespassing of one or more entrances to the isolation, preferably the monitoring is logged for later review. In case the isolation is an industrial/commercial kitchen the entrances may be doors and windows. Said doors and windows may continuously be monitored for trespassing, e.g. by use of conventional motion sensors or similar means, so that the user is assured that any trespassing by a person during the disinfection step will not only be prevented, but also that an attempt to enter the room may be detected, so that all necessary actions can be carried out. Said entrances may initially be closed and locked, but it is not a requirement. In case the isolation is a large air conditioning system the entrances may be some or all inlets/outlets to the system. In this case a trespassing is probably not possible for the majority of the entrances, for which reason there is no need for monitoring trespassing for all entrances except maybe the main entrance or the entrances to the room(s) in which the system is placed/associated to.

Preferably the monitoring is logged for later review e.g. on a memory device known in the art. The user can thus at a later time enter the memory containing the logged monitoring and reviewing when the isolation was trespassed and which consequences the trespassing had. More preferably, the entire disinfection method is monitored and logged so that the user at a later time can review how the different steps in the entire disinfection method were carried out.

The securing step may comprise continuously removing air and/or oxygen from the isolation for creating an underpressure in said isolation. A ventilator or pump may be used to move the air or oxygen to an area in the surroundings where it is safe to release the ozone, for example the surrounding air outside the building containing the isolation. Having an underpressure in said isolation will help to prevent ozone from escaping to the surroundings and thus possibly harm the persons located near the isolation. The moving of air or oxygen must take place at a rate lower than the rate of generation of ozone, so that the ozone will be present in the entire isolation.

As the isolation can be any room which either comprises surfaces requiring disinfection, or air needing to be sterilised, air will be present in the isolation. Extra oxygen, however, may be presented in the isolation from a pressure tank containing oxygen or from an oxygen generator or similar. The extra oxygen can be used to vary the amount of ozone generated, and accordingly the speed of the method according to the invention. During the securing step it thus may be necessary to remove air and/or oxygen, for creating an underpressure in said isolation, in order to prevent ozone from escaping to the surroundings.

If unauthorised access to the isolation i.e. trespassing, is detected, the securing step can further comprise one or more of the following actions. Terminating the generation of ozone, giving a warning alarm, and evacuating the isolation for removal of excess ozone from air and/or oxygen present in the isolation. It is thus not a requirement that all said three actions are performed, only that the environment in the isolation is not hazardous to the trespasser and one or two actions may be sufficient. When trespassing is detected it can of course be a huge advantage to terminate the generation of ozone, as a person thus most likely has opened an entrance to the isolation and entered the isolation. To minimise the amount of ozone exposed to the person the generation of ozone must preferably be stopped immediately. Detecting a trespassing does of course not necessarily mean that a person has entered the isolation, he might only have opened an entrance shortly, but to be sure the ozone generation should preferably be terminated. Alternatively, the generation of ozone is terminated until it is detected that the person has left the isolation or is not present in the isolation, e.g. by having motions sensors or other similar means, present in or in the vicinity of the isolation. In case of trespassing it can also be advantageous that the apparatus gives a warning alarm. Said alarm can be any kind of alarm arranged for informing both the trespasser and the person supervising the disinfection/sterilisation method, but preferred alarms comprises one or more of audio, visual or electronic alarms, the electronic alarm for example being transmitted via Wifi or as an SMS. The person trespassing and preferably also the user of the apparatus are thus alarmed that the person has put himself in danger by opening an entrance to the isolation. Hopefully the person will react on the alarm and leave the isolation immediately, and the user will be aware that a person may need help, or that the ozone generation has been terminated and may have to be restarted. In case the person remains in the isolation, the concentration of ozone in the isolation must be reduced as quickly as possible after a trespassing is detected advantageously by removing the ozone from the isolation. The evacuation can preferably be done via an existing ventilation system in the isolation or alternatively via a ventilating system in the apparatus with an outlet leading to a proper area in the surroundings. Removing excess ozone from oxygen present in the isolation, can be especially preferred when extra oxygen from e.g. a pressure tank or an oxygen generator has been added to the air in the isolation to increase the generation of ozone. The monitoring is preferably logged, in order to review the memory containing the logged monitoring at a later time and thus review when the isolation was trespassed and which consequences the trespassing had.

In another embodiment the method can furthermore comprise initiating a control unit arranged for controlling the time of disinfection, the control unit preferably comprising at least one timer for measuring a predetermined time interval and/or at least one sensor for measuring the concentration of ozone. Having a control unit can help to automate the disinfection method, e.g. by controlling the time of disinfection, that is, the time necessary for disinfecting all surfaces in the isolation. The user does therefore not have the responsibility of e.g. timing the period of generating ozone, measuring whether the surfaces have been disinfected or measuring the ozone concentration. The control unit does it automatically. The control unit can preferably comprise at least one timer for measuring a predetermined time interval and/or at least one sensor for measuring the concentration of ozone. The timer can be applied when for example the period of generating ozone is to be timed, as can be an advantage for ensuring that ozone is only generated for a limited time interval, and thus in a limited amount. Similarly, the at least one sensor can be applied in measuring the concentration of ozone in the air in the isolation, which is an advantage in determining when a sufficient amount of ozone has been added to the air, i.e. that the surfaces in the isolation has been disinfected. It can thus be an advantage that initiating the control unit comprises starting the timer, and/or that initiating the control unit comprises continuously monitoring the ozone concentration in said isolation with the at least one sensor, so that the timer and/or sensor are automatically started. The disinfection step can thus begin and proceed immediately and automatically so that the duration of the entire disinfection method is minimised. However, the disinfection step can be controlled manually instead, if wanted or by a combination of manual and automatic controlling.

Advantageously, the termination step can comprise that the control unit turns off the ozone generation, when a predetermined time interval measured by the timer has elapsed. The predetermined interval is preferably between 0 minutes and hours though depending on the ozone concentration in the isolation. Alternatively, the termination step can comprise that the control unit turns off the ozone generation, after the at least one sensor has measured a predetermined concentration of ozone in said isolation for a predetermined time interval measured by the timer. For both cases the termination step is automated thus resulting in a faster and more precise disinfection process, and for the user less time consuming disinfection process, as the user only has to start the disinfection method. As written previously it is of course within the scope of the present invention that the disinfection step can be controlled manually if wanted, as is also the case with the termination and securing step.

In this respect the controller can also advantageously combine the use of the timer and the sensor during both the disinfection step and the termination step. In one example the timer can measure a predetermined time interval for ozone generation during the disinfection step, and the sensor can monitor the afterwards fall in ozone concentration so that the securing step is maintained until it is safe to re-enter the isolation, i.e. until the ozone concentration is below an ozone threshold value again (<0.1 ppm). In another example the sensor can monitor the rise in ozone concentration after initiating the disinfection step. When a predetermined ozone concentration is achieved the timer can measure a predetermined time interval for maintaining the achieved ozone concentration, and afterwards when the ozone generation is terminated the sensor can monitor the fall in ozone concentration so that the securing step is maintained until the ozone concentration is below said ozone threshold value, i.e. it is safe to re-enter the isolation. As previously stated, the different steps of the entire disinfection method and thus also the operation of the timer and sensor may be monitored and logged so that the user at a later time can review how the different steps in the entire disinfection method was carried out. This is especially advantageous as the method according to the invention can be optimised whereby it not only will be more effective but also less expensive.

Advantageously, said one or more surfaces can have been in contact with foodstuff. Especially within the food industry the hygienic requirements are high. All surfaces which have been in contact with foodstuff must thus be cleaned thoroughly after use. Conventional cleaning e.g. with water and soap is very effective, however surfaces that are difficult to reach or have a limited surface area can be difficult to clean and disinfect sufficiently. The disinfection method of the present invention which applies ozone as disinfection agent is effective in cleaning said surfaces which are difficult to reach or have limited surface area due to ozone's size and mobility.

In a preferred embodiment of the present invention it can be an advantage to have an apparatus for disinfecting surfaces and/or sterilizing air, wherein the apparatus comprises one or more UV light sources, arranged for generating ozone, at least one means for circulating air and/or added oxygen, means for controlling the operation of the apparatus and for logging the operation of the apparatus, communication means for communicating with the means for controlling the operation of the apparatus, said communication preferably being transmitted wirelessly or by hard wire and that the apparatus comprises a securing means, arranged for securing isolation of the surfaces to be disinfected from the surroundings.

It is a considerable advantage if the apparatus for disinfecting surfaces comprises a securing means, arranged for securing isolation of the surfaces to be disinfected from the surroundings. Having a securing means that provides an isolation of the surfaces to be disinfected from the surroundings ensures that only the area containing said surface are exposed to ozone during the disinfection. A person not being aware that a disinfection process has been started, does thus not risk by accident being exposed to the ozone, but is rather prevented from entering. The securing means thus provides a disinfection process that is safe to use, i.e. ensures that the user and people in the vicinity are not put in risk of being exposed to ozone. The securing means also result in that the user can start the disinfection method without keeping constant supervision, as the user knows that the securing means guarantees safe operation.

In an embodiment the securing means can comprise means for locking one or more entrances to the isolation. This can be preferable especially in the cases where the isolation is a room and where one or more of the entrances are doors. When starting the apparatus the doors can thus automatically be locked. The user thus knows that other persons can not enter the isolation by accident. A deliberate action of unlocking the locked doors has to be done for being exposed to the ozone. Preferably a visual alarm is attached to the entrances, such that other persons easily can see that the room is being disinfected. In a preferred embodiment said visual alarm comprises a timer, such that it is possible to see when the disinfection is terminated and when the room again can be safely entered.

In another embodiment the securing means can comprise means for detecting trespassing of the one or more entrances, and for acting accordingly by performing at least one of terminating the generation of ozone, giving an alarm, and evacuating the isolation for removal of excess ozone from air and/or added oxygen present in the isolation. It is thus not a requirement that all said three acts is performed, only that the environment in the isolation is not hazardous to the trespasser and one or two acts may be sufficient. Opening the doors during disinfection is hazardous if no underpressure has been created in the isolation. It is thus advantageous to detect if somebody is trespassing doors that may be closed or locked, but also to detect if somebody is trespassing other entrances to the isolation such as windows or airshafts. Precautions can be made to minimise the danger put to the person trespassing. Obviously, a termination of the generation of ozone is wise, such that the ozone concentration can be reduced and only minimal amounts of ozone can diffuse to the surroundings in case no underpressure has been created in the isolation. Giving an alarm will help to warn the person trespassing that he is putting himself into danger, but will hopefully also inform the user that the disinfection process has been interrupted and that somebody may need help. Finally, a way of minimising the amount of ozone being exposed to the trespassing person and/or diffusing to the surroundings is to have the securing means preferably evacuates the isolation and thus remove excess ozone from air or oxygen present in the isolation. The evacuation can e.g. be carried out via a ventilation system already present in the isolation, which is in communication with the securing means, but it can also be carried out via a ventilation system present in the apparatus, a ventilation system already present in the room or with an exhaust made specifically for this purpose.

In yet another embodiment the securing means can communicate with a separate securing means for the isolation. In the event that the isolation for example is a storage/cooling room for foodstuff, a securing means may already exist. The securing means may for example automatically lock the door to the room, and start cooling and/or air conditioning, when the door is closed, and require a password to unlock the door again. The apparatus of the present invention may be installed in the room or in connection with the room, with the control unit being in communication with the securing means of the room. The disinfection method may be programmed to start every time the door is closed and locked, or alternatively every time the door is closed and locked and the user initiates the disinfection method. If the door is opened either by typing in a password or by force, the control unit can receive signal from the securing means of the room and immediately terminate the generation of ozone, and possibly start, maintain or increase evacuation of the isolation to minimise the amount of ozone being exposed to the trespassing person and/or the surroundings.

Advantageously, the one or more UV light sources can emit UV radiation with a wavelength in the vicinity of 100 nm to 280 nm, preferably the wavelength is about 185 nm, as UV light with a wavelength in the vicinity of 100 nm to 280 nm has proven effective in producing ozone from the oxygen. Preferably, the one or more UV light sources applied emit UV radiation with a wavelength of about 185 nm as said specific wavelength has proven particularly suited to the inventors of the present invention for producing ozone.

Advantageously, the apparatus can further comprise a timer arranged for measuring a predetermined time interval. Preferably, the apparatus can further comprise a sensor arranged for continuously monitoring the ozone concentration in said isolation. As described previously having a timer and/or a sensor can help to automate the disinfection and as a consequence to minimise the time used on the disinfection, as the user does not have to supervise and manually control the different steps of the disinfection method. Furthermore, it can as previously described be preferred to combine the use of a timer and a sensor for controlling the disinfection, e.g. to monitor with the sensor the increase of ozone up to a predetermined concentration, hold said predetermined ozone concentration for a predetermined time interval measured by the timer, terminate the ozone generation, and monitor with the sensor the drop in ozone concentration down to a predetermined concentration, before terminating the securing step.

In an especially preferred embodiment the apparatus according to the invention can be placed in or in connection with an existing ventilation system, connected to the isolation, as ventilation systems can be difficult to access and thus disinfect after installation. Placing the apparatus inside the ventilation system ensures that the user does not have to install the apparatus each time a disinfection is wanted, which may be difficult, though of course depending on the exact shape and placement of the ventilation system. Furthermore, placing the apparatus inside the ventilation system means that the apparatus does not require space outside the ventilation system, space that very well is already reserved for something else. In a preferred embodiment, the apparatus is placed in connected with an existing ventilation system, so that ozone can be generated in the apparatus from air flowing in the ventilation system. Additionally, extra ozone can be generated from oxygen contained in a pressure tank or from an oxygen generator and afterwards added to the air inside the ventilation system.

The apparatus can be placed permanently in the isolation or can be transported to the isolation. In case the isolation has to be disinfected and/or sterilized often it can be advantageous that the apparatus is placed permanently in the isolation. The apparatus can thus for example be initiated each night after all people have left the area to be disinfected and/or sterilized. In one embodiment, it can be advantageous if the apparatus according to the invention is transportable, so that the apparatus can be transported to the areas in need of being disinfected and/or sterilized. This may be advantageously for areas which need less frequent disinfection/sterilisation. Furthermore, when the apparatus is transportable it does thus not take up space constantly in the areas to be disinfected and/or sterilized, and can be used for disinfecting and/or sterilizing several areas and not only one area. For both embodiments the possible evacuation of the isolation can be carried out via a ventilation system included in the apparatus. Additionally, extra ozone can be generated from oxygen contained in a pressure tank or from an oxygen generator and afterwards added to the air in the isolation.

In a preferred embodiment the one or more UV light sources can be shielded so that said sources are not visible to a person entering the isolation during operation of the apparatus. Depending on the wavelength of the UV radiation the radiation can cause damage to humans. Directing UV-C radiation at the human body can cause erythema (redness of the skin; sunburn) and/or conjunctivitis (inflammation of the connective tissue). The one or more UV light sources should thus be shielded the best way possible from the user and any other persons in the vicinity of the apparatus during disinfection. One possible way to shield is by placing the one or more UV light sources inside a box or behind a cover preferably also shielding other components of the apparatus, such as the at least one means for circulating air and the means for controlling the operation of the apparatus. The box or cover should have at least one inlet and one outlet for moving air or oxygen into contact with the UV radiation and releasing the air or oxygen now containing a large amount of ozone to the isolation again. In the embodiment where the apparatus is placed in an existing ventilation system, connected to the room, the apparatus may not necessarily have to be shielded from the surroundings.

The apparatus can furthermore comprise one or more UV light sources, arranged for emitting UV-light capable of sterilizing air. The UV light source preferably emits radiation with a wavelength in the vicinity of 253.7 nm, which is known to sterilize air. The UV light source can thus emit radiation arranged both for disinfecting surfaces and for sterilizing air in the isolation while simultaneously having securing means monitor trespassing. If the isolation for example is a room containing vegetables and/or fruits said combination of UV radiation can minimise ethylene concentration by photochemical oxidation and thus e.g. minimise decomposition. In case the UV light source is shielded, i.e. a person cannot be directly subjected to the UV-light, the sterilization of air using UV-light at a wavelength which does not produce hazardous amounts of ozone, i.e. in the vicinity of 253.7 nm, could also happen in a room where no securing has been initiated.

Advantageously the apparatus can furthermore comprise one or more means for emitting ultra sound. The one or more means can for example be directed in multiple directions thus emitting ultra sound in multiple directions, which for example can be used to destroy bacteria contained in silicon.

The method of disinfecting one or more surfaces and/or sterilizing air, and apparatus for use in the method may be modified in that the method or apparatus comprises one or more LED lamps instead of one or more UV-lamps. Combinations of UV lamps and LED lamps are also foreseen within the scope of the present invention. LED lamps can produce UV radiation at wavelengths which can be used for producing ozone and/or for sterilizing air, and are considered especially advantageous as said lamps use only very low amounts of energy, and accordingly the apparatus and method according to the invention will be especially economical to carry out. Materials used for producing LED lamps can for example be, but is not limited to aluminium nitride (210 nm) and boron nitride (215 nm).

The apparatus may comprise one or more LED lamps and one or more UV-lamps in combination for generating ozone and/or for sterilizing air, as a combination may be advantageous e.g. due to space requirements, costs, developments in energy efficiency and similar.

The present invention further relates to the use of the method and the apparatus according to the present invention for disinfecting surfaces and/or sterilizing air in industrial kitchens or for disinfecting surfaces and/or sterilizing air locating in productions for foodstuff or the pharmaceutical sector, or for disinfecting surfaces and/or sterilizing air in medical areas or public buildings.

The method of carrying out the present invention and the structure of the preferred device for use in the method will be described in more detail below with reference to exemplary embodiments shown in the drawings, wherein,

EXAMPLES

The invention is described below with the assumption that the apparatus according to the present invention is placed in or in connection with an existing air ventilation system and for disinfecting a production facility for example in the fishing industry. However, this assumption is not to be construed as limiting, and the apparatus can just as easily be placed at other locations and used for different disinfections purposes.

Figure 1:
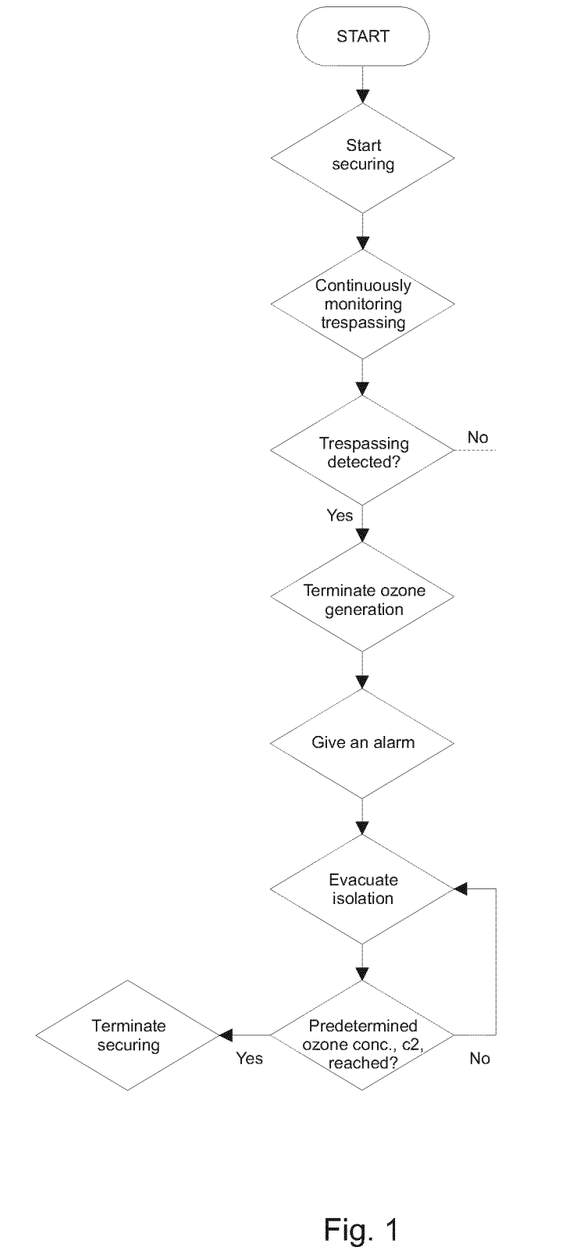
FIG. 1 shows a flow chart diagram for the case where a person trespasses the secured isolation during the method of disinfecting one or more surfaces and/or sterilizing air.

FIG. 1 shows a flow chart diagram for the case where a person trespasses the secured isolation during the method of disinfecting one or more surfaces. The method comprises initially starting the apparatus, preferably by use of a remote control, after closing all entrances to the area to be isolated, in the present case the production facilities in the fishing industry. The apparatus thus initiates the securing step which preferably comprises creating an underpressure in the isolation and that the securing means continuously monitors trespassing of one or more entrances to the isolation, preferably by use of motion sensors. The case where no trespassing is detected will be shown in FIG. 2. On the other hand, if the securing means detects trespassing it terminates the generation of ozone, i.e. shuts off power to the UV-C lamps. An alarm is given which preferably comprises giving both an audio signal and a signal to the remote control so that the user is aware that someone is trespassing the isolation and thus may be in danger. Simultaneously the isolation is evacuated either by the control unit of the apparatus communicating with a ventilation system already present in the isolation, or by use of the means for circulating air and/or added oxygen, e.g. a ventilator, which is connected to a tube with an outlet placed outside the isolation. The evacuation is maintained as long as a predetermined ozone concentration c2 (e.g. 0.1 ppm) measured by a sensor has not yet been reached. The securing step is terminated, when said concentration c2 is reached.

Figure 2:
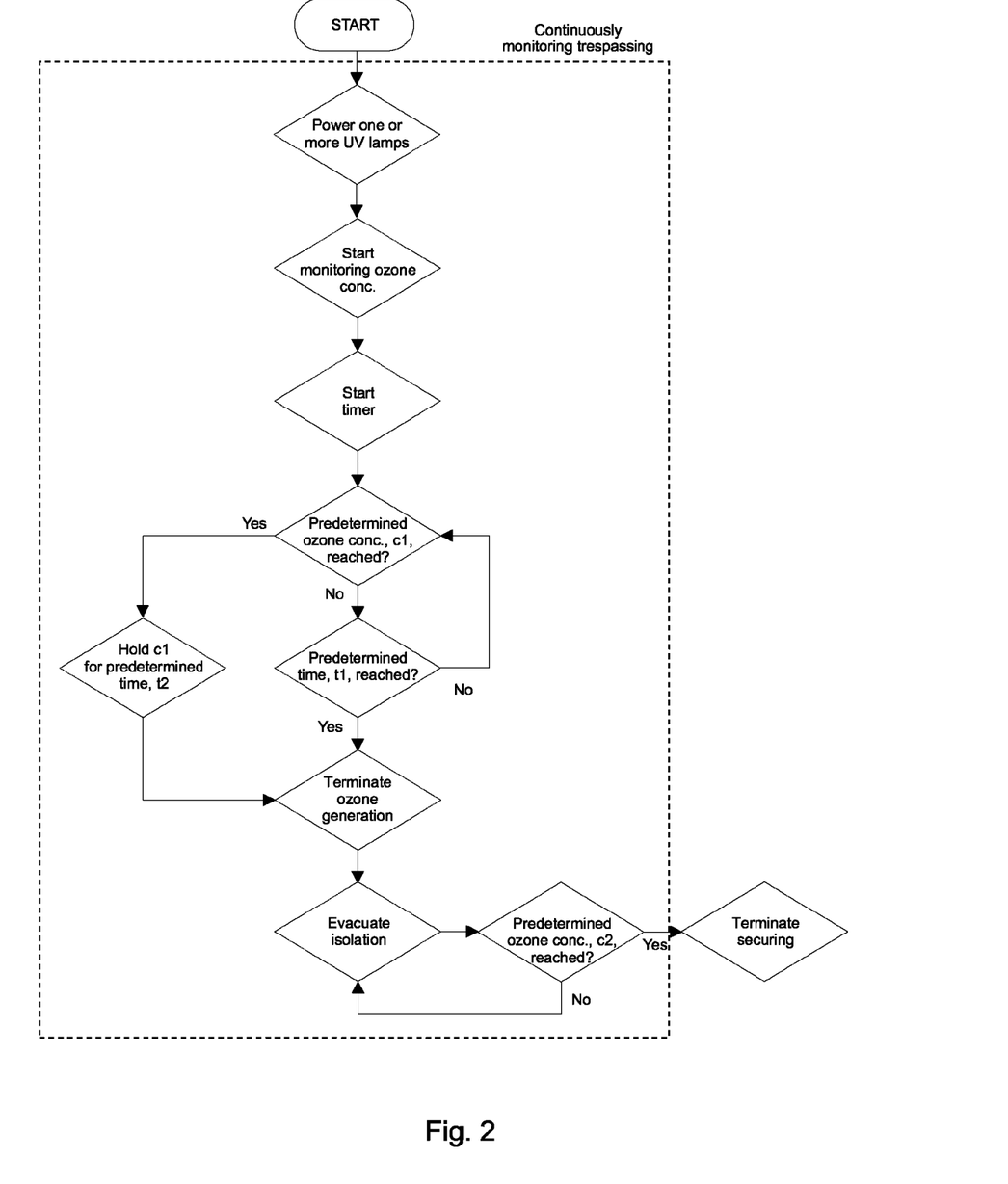
FIG. 2 shows a flow chart diagram for an exemplary method of disinfecting one or more surfaces and/or sterilizing air in the case where no trespassing is detected.

FIG. 2 shows a flow chart diagram for an exemplary method of disinfecting one or more surfaces in the case where no trespassing is detected. Starting the apparatus also comprises powering one or more UV lamps for generating ozone from oxygen in the air present in the isolation or from an external oxygen source. A sensor monitors the concentration of ozone present in the air until a predetermined concentration c1 is reached, and a timer is started and measures a predetermined time interval, t1 , being the maximum acceptable period for generating ozone. In case the predetermined ozone concentration c1 is reached before the predetermined time interval t1 expires, said concentration is maintained for a predetermined time interval t2 measured by the timer, after which the ozone generation is terminated. On the other hand, if the predetermined time interval t1 expires before the predetermined ozone concentration c1 is reached, the generation of ozone is terminated. The isolation is evacuated either by the control unit of the apparatus communicating with a ventilation system already present in the isolation, or by use of the means for circulating air and/or added oxygen, e.g. a ventilator, which is connected to a tube with an outlet placed outside the isolation. The evacuation is maintained as long as a predetermined ozone concentration c2 (e.g. 0.1 ppm) measured by the sensor has not yet been reached. The securing step is terminated, when said concentration c2 is reached.

The apparatus according to the invention has a simple and inexpensive design, and can therefore be used equally well for both privately and in kitchens or hospital facilities where known disinfections apparatuses are too troublesome and complicated to use.

Modifications and combinations of the above principles and designs are foreseen within the scope of the present invention.

What is claimed is:

1. Method of disinfecting one or more surfaces and/or sterilizing air comprising:
   creating an isolation comprising the surfaces to be disinfected,
   conducting a disinfection step by emitting UV radiation for the generation of ozone from one or more ultra violet (UV) light sources and adding the generated ozone to said isolation,
   terminating the generation of ozone in a termination step after the disinfection is complete, and
   providing a securing step wherein trespassing of one or more entrances to the isolation is continuously monitored during the disinfection step,
   wherein when trespassing is detected, the securing step further comprises terminating the generation of ozone, generating an alarm, and evacuating the isolation by removing excess ozone from air and/or oxygen that is present in the isolation.

2. Method of disinfecting one or more surfaces and/or sterilizing air according to claim 1, wherein the disinfection step further comprises emitting UV radiation for the sterilization of air from one or more ultra violet (UV) light sources.

3. Method of disinfecting one or more surfaces and/or sterilizing air according to claim 1, wherein the monitoring of trespassing is logged for later review.

4. Method of disinfecting one or more surfaces and/or sterilizing air according to claim 1, wherein the terminating of the generation of ozone when a trespassing is detected occurs before the disinfection step is completed with the securing step comprises continuously removing air and/or oxygen from the isolation for creating an underpressure in said isolation at that time.

5. Method of disinfecting one or more surfaces and/or sterilizing air according to claim 1, wherein the method of disinfecting one or more surfaces furthermore comprises initiating a control unit arranged for controlling the time of disinfection, the control unit preferably comprising at least one timer for measuring a predetermined time interval and/or at least one sensor for measuring the concentration of ozone.

6. Method of disinfecting one or more surfaces and/or sterilizing air according to claim 5, wherein initiating the control unit comprises starting the timer.

7. Method of disinfecting one or more surfaces and/or sterilizing air according to claim 1, wherein initiating the control unit comprises continuously monitoring the ozone concentration in the air in said isolation with the at least one sensor.

8. Method of disinfecting one or more surfaces and/or sterilizing air according to claim 1, wherein the termination step comprises that the control unit turns off the ozone generation, when a predetermined time interval measured by the timer has elapsed.

9. Method of disinfecting one or more surfaces and/or sterilizing air according to claim 1, wherein the termination step comprises that the control unit turns off the ozone generation, after the at least one sensor has measured a predetermined concentration of ozone in said isolation for a predetermined time interval measured by the timer.

10. Method of disinfecting one or more surfaces and/or sterilizing air according to claim 1, wherein said one or more surfaces have been in contact with foodstuff.

11. A method according to claim 1, wherein the UV light sources are one or more light-emitting diodes (LEDs).

12. An apparatus for disinfecting surfaces and/or sterilizing air, the apparatus comprising:
   one or more UV light sources, arranged for generating ozone,
   at least one means for circulating air and/or added oxygen,
   means for controlling the operation of the apparatus and for logging the operation of the apparatus,
   communication means for communicating with the means for controlling the operation of the apparatus, said communication preferably being transmitted wirelessly or by hard wire, and
   securing means, arranged for securing isolation of the surfaces to be disinfected from the surroundings, said securing means comprises means for detecting trespassing of the one or more entrances, and for acting accordingly when trespassing is detected by means for terminating the generation of ozone, means for generating an alarm, and means for evacuating the isolation by removing excess ozone from air and/or added oxygen that is present in the isolation.

13. An apparatus for disinfecting surfaces and/or sterilizing air according to claim 12, wherein the securing means can communicate with a separate securing means already existing for the isolation.

14. An apparatus for disinfecting surfaces and/or sterilizing air according to claim 12, wherein the one or more UV light sources emit UV radiation with a wavelength in the vicinity of 100 nm to 280 nm.

15. An apparatus for disinfecting surfaces and/or sterilizing air according to claim 12, wherein the apparatus further comprises a timer arranged for measuring a predetermined time interval.

16. An apparatus for disinfecting surfaces and/or sterilizing air according to claim 12, wherein the apparatus further comprises a sensor arranged for continuously monitoring the ozone concentration in said isolation.

17. An apparatus for disinfecting surfaces and/or sterilizing air according to claim 12, wherein the apparatus is placed in or in connection with an existing ventilation system, connected to the isolation.

18. An apparatus for disinfecting surfaces and/or sterilizing air according to claim 12, wherein the apparatus is placed permanently in the isolation or is transported to the isolation.

19. An apparatus for disinfecting surfaces and/or sterilizing air according to claim 12, wherein the one or more UV light sources are shielded so that said sources are not visible to a person entering the isolation during operation of the apparatus.

20. An apparatus for disinfecting surfaces and/or sterilizing air according to claim 12, wherein the apparatus furthermore comprises one or more UV light sources, arranged for emitting UV-light capable of sterilizing air.

21. An apparatus for disinfecting surfaces and/or sterilizing air according to claim 12, wherein the means for generating an alarm comprises one or more means for emitting ultra sound and the means for terminating of the generation of ozone when a trespassing is detected occurs before the disinfection step is completed and comprises means for creating an underpressure in said isolation at that time.

22. An apparatus according to claim 12, wherein the UV light sources are one or more light-emitting diodes (LEDs).

23. An apparatus for disinfecting surfaces and/or sterilizing air according to claim 12, wherein the apparatus comprises one or more LED lamps and one or more UV light sources in combination for generating ozone and/or for sterilizing air.

* * * * *